United States Patent
Pfeiffer et al.

[11] Patent Number: 5,899,860
[45] Date of Patent: May 4, 1999

[54] METHOD AND DEVICE FOR DETERMINING THE POSITION OF A CATHETER INSIDE THE BODY OF A PATIENT

[75] Inventors: Georg Pfeiffer, Djursholm; Bruno Slettenmark, Järfälla, both of Sweden

[73] Assignee: Siemens Elema AB, Solna, Sweden

[21] Appl. No.: 08/919,209

[22] Filed: Aug. 28, 1997

[30]  Foreign Application Priority Data

Sep. 12, 1996 [SE] Sweden ................................. 9603314

[51] Int. Cl.$^6$ ................................................. A61B 19/00
[52] U.S. Cl. ........................................... 600/424; 600/427
[58] Field of Search ................................. 600/424, 300, 600/373, 374, 425, 427; 128/899; 607/122

[56] References Cited

U.S. PATENT DOCUMENTS 5,042,486  8/1991  Pfeiler et al. .......................... 600/424
5,722,402  3/1998  Swanson et al. ....................... 600/374
5,776,064  7/1998  Kalfas et al. .......................... 600/429

*Primary Examiner*—Ruth S. Smith
*Attorney, Agent, or Firm*—Hill & Simpson

[57]  ABSTRACT

In a method and apparatus for determining the position of a catheter inside the body of a patient, position signals are transmitted between the catheter and a position location unit, located at a distance from the catheter, the position signals are transmitted during a calibration stage from known calibration positions inside the body, or position signals, transmitted by the position location unit, are received at the known calibration positions. A correction function is determined from the difference between the calibration positions derived from the received location signals and the known, true calibration positions, whereupon catheter positions, derived from received position signals, are corrected in subsequent measurement stages according to the correction function.

39 Claims, 1 Drawing Sheet

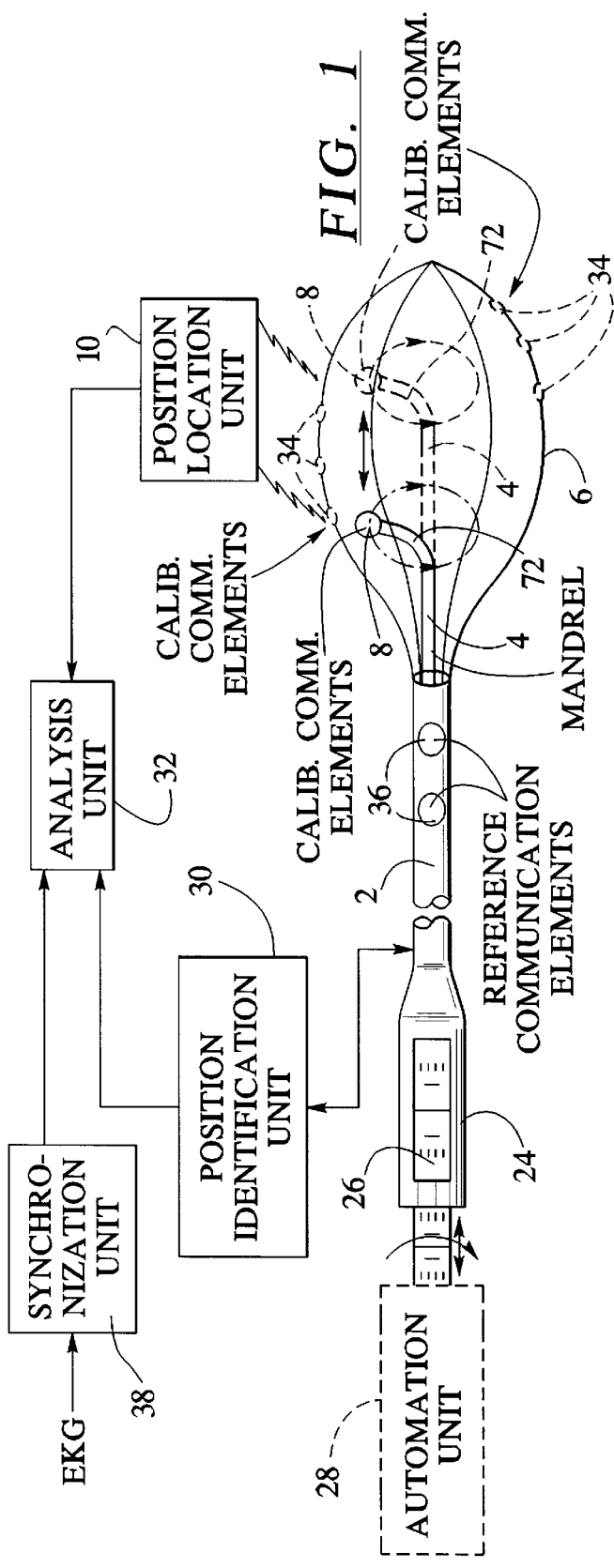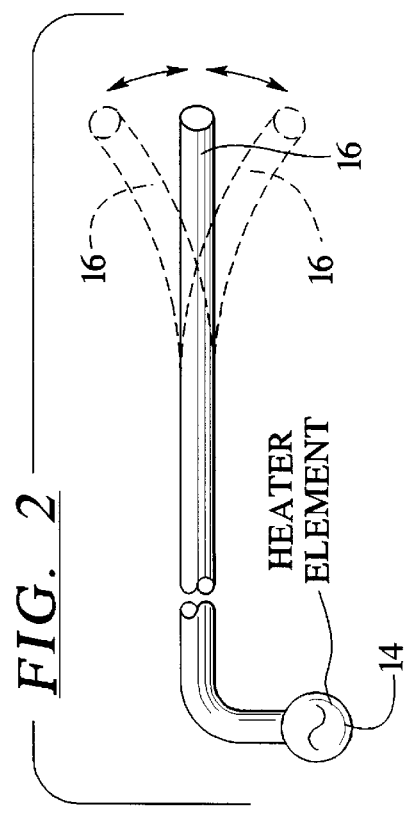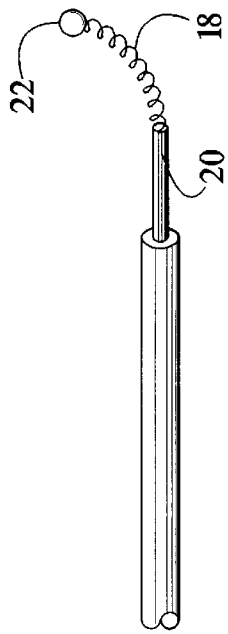

METHOD AND DEVICE FOR DETERMINING THE POSITION OF A CATHETER INSIDE THE BODY OF A PATIENT

BACKGROUND OF THE INVENTION

1. Field of the Invention

The present invention relates to a method and apparatus for determining the position of a catheter inside the body of a patient from position signals transmitted between the catheter and a remote position location unit.

2. Description of the Prior Art

For determining the position of e.g. the tip of a catheter inside the body (i.e. an endoceliac catheter), for example in a blood vessel or a cavity of the heart, or in the imaging of internal organs by mapping, the heterogeneity and, accordingly, the varying physical properties of adjacent tissues and even the presence of other objects in or outside the body can cause distortion, to a greater or lesser degree, in position determination or geometry depiction. This effect can be considerable in the use of ultrasound because of e.g. variation in the density of tissues and the velocity of sound. If electromagnetic methods are used, the variation in e.g. electrical conductivity, relative permittivity and relative permeability can affect measurement accuracy.

In non-medical applications, such as astronomy and remote sensing, corrections can be made for both constant and time-related aberrations in the atmosphere and measuring system by observing a reference object with a known shape in the ray path or close to the observed object.

In the brochure "A new method for non-fluoroscopic catheter based endocardial mapping", published by Ben-Haim et al., a technique is described for endocardial mapping with a non-fluoroscopic catheter in which a number of radiographs are first taken of a heart catheter located in a number of different positions in a ventricle of a heart.

SUMMARY OF THE INVENTION

An object of the present invention is to facilitate accurate determination of the position of a catheter inside the body without the use of ionizing radiation.

The above object is achieved in accordance with the invention in a method and apparatus for detecting a position of a catheter when inside a body of a patient wherein, in a calibration phase, signals are transmitted between a number of known calibration positions of the catheter in the body cavity and an position locator. The position locator thus obtains a number of apparent calibration positions which are respectively associated with the known calibration positions, but deviate therefrom due to passage of the signals through body tissue. In the calibration phase, a correction function is generated at the position locator, or in a computer connected thereto, from the deviation of the apparent calibration positions from the known calibration positions. Any further signals which are transmitted between the catheter and the position locator, such as during a medical procedure involving the catheter in the body cavity, are corrected using the correction function, so that the actual position of the catheter in the body cavity is identified.

The aforementioned signals can be transmitted from transmitters located on the catheter to receivers located at the position locator, or the signals can be transmitted from transmitters located at the position sensor to receivers located at the catheter.

In the method and device according to the invention, a correction function, subsequently utilized for correcting measurement data in position determination and for correcting image data in mapping, is accordingly determined. Correct position determination and correct geometry are therefore attained with use of a correction function determined by having a catheter, or the tip of a catheter, perform a known movement inside a cavity in the body at the same time as the position of the catheter is determined from position signals sent and received between the catheter and remote position location means.

According to one embodiment of the method of the invention, position signals are transmitted from or are received at the catheter tip to allow determination of the position of the tip, normally the most important part of the catheter in this context.

According to another embodiment of the method of the invention, a wire basket or balloon is deployed at the tip of the catheter, and measurements are performed during the calibration stage with the tip of the catheter inside the space enclosed by the basket or balloon, whereupon the basket or balloon is collapsed and the diagnostic and/or therapeutic procedure, such as mapping of the cavity's interior walls, sensing and/or stimulation of electrical activity in body tissue, ablation and or pressure measurement, is performed. During this procedure, the positions of the tip of the catheter, as determined by the position signals, are corrected with the correction function. This creates an unimpeded space, inside of which the catheter can be moved without touching tissue, for the calibration stage, so the catheter cannot be deformed and, accordingly, assume "erroneous" positions.

According to further embodiments of the device of the invention, the catheter has a flexible, tubular outer sleeve enclosing a sliding and rotating mandrel in whose tip a transmitter or receiver is arranged. The distal end section of the mandrel is appropriately made of a resilient material and is pre-bent, or is a curved coil spring arranged on the distal end of the mandrel, the catheter transmitter or receiver being arranged at the free end of the curved coil spring. The mandrel's end section alternatively made of a memory alloy, and a means is provided for electrically heating the end section in order to bend it. The mandrel's end section can also be devised with a mechanical joint to permit bending of the end section. At the catheter end located outside the body, an arrangement is provided for sliding and/or rotating the mandrel in relation to the sleeve. The end of the curved end section thereby describes a cylindrical area when the mandrel is linearly displaced and rotated at the same time.

According to another embodiment of the device of the invention, the sliding and/or rotating arrangement is motorized, and a transducer is arranged for automatic reading of the mandrel's movement and control of the drive motor on the basis thereof. In this manner, the mandrel's determined movement is fed back to the drive motor in order to control the motor and to cause the mandrel to perform the desired movement.

If the position location unit is outside the patient's body, or in the patient at a relatively long distance from the measurement catheter, compensation must be made for movement between the measurement catheter and the position location means caused by the patient's breathing or other movements. According to another embodiment of the device of the invention, a reference receiver or transmitter is therefore arranged on the sleeve of the catheter to serve, in concert with the catheter transmitter or receiver, as an internal reference in compensating for the patient's breathing and other movements.

DESCRIPTION OF THE DRAWINGS

FIG. 1 shows an exemplary embodiment of the device according to the invention, with a basket catheter.

FIGS. 2 and 3 respectively illustrate two ways to achieve a curved section on the distal end of the mandrel.

DESCRIPTION OF THE PREFERRED EMBODIMENTS

FIG. 1 shows an embodiment of the device according to the invention, with a basket catheter containing a flexible, tubular catheter sleeve 2 inside of which a mandrel 4 and an expandable element such as a wire basket 6 are retracted during the catheter's insertion into the patient's body. A catheter communication element, such as transmitter 8, is arranged at the end of the mandrel 4 to transmit location signals, intended for reception by position location unit in the form of a receiver unit 10, arranged at a distance from the tip of the catheter, preferably outside the patient's body. The communication element can alternatively be a catheter receiver arranged at the tip of the mandrel 4 to receive signals from the position location unit 10 in the form of a transmitter unit. When the mandrel 4 is in the retracted position, the catheter transmitter or receiver 8 is in the opening of the catheter sleeve 2.

When the catheter is in position inside the patient, the wire basket 6 is deployed outside the catheter sleeve 2. The basket 6 is made of e.g. metal wire, carbon fiber or a polymer material, and is resilient so it expands when deployed outside the catheter sleeve 2.

When the catheter has been accordingly inserted into a cavity in the patient's body, the expanded basket 6 fills the cavity in whole or in part and is affixed therein. The basket 6 therefore keeps its interior separated from body tissue, enabling the catheter tip therein to describe the desired movement without touching wall tissue or any other mechanical impediment.

In the "starting position", the catheter transmitter or receiver 8 is in the mouth of the catheter sleeve 2. When the tip of the catheter is in position, e.g. in the ventricle of a heart, the catheter transmitter or receiver 8 can be deployed outside the catheter sleeve 2 with the mandrel 4.

The end section 12 of the mandrel 4 can be pre-bent so the catheter transmitter or receiver 8 describes a circular movement when the mandrel 4 is rotated. When the mandrel 4 is axially displaced at the same time as it is rotated on its axis, the catheter transmitter and/or receiver 8 will describe a cylindrical movement.

In order to achieve the curved end section 12 of the mandrel, the end section can, as noted above, be pre-bent or alternatively can be made of a memory alloy, such as NiTi, and a heater element 14 is provided for electrically heating the end section 16 so as to bend it, as shown in FIG. 2.

According to another alternative, a curved coil spring 18 is arranged on the distal end of the mandrel 20, the catheter transmitter or receiver 22 being arranged on the free end of the spring 18, as shown in FIG. 3. The advantage of the latter embodiment is that the load on the material is reduced and, accordingly the risk of fatigue is also reduced.

The mandrel's end section can also be devised with a mechanical joint to allow bending of the end section into the desired shape.

The proximal end of the catheter is intended to be outside the patient's body, and a manipulator 24 is arranged on this end for displacing and/or rotating the mandrel 4 in relation to the sleeve 2. This movement of the mandrel 4 can be manual, and scales (indicators) 26 are arranged to permit the reading of the magnitude of the displacement and rotation. This part of the catheter can be made with dimensions facilitating manipulation of the mandrel 4 and reading of the scales 26.

Movement of the mandrel 4 can also be automated by means of appropriate actuators arranged in an automation unit 28. These motorized actuators are accordingly connected to the mandrel 4 in order to displace and rotate it in relation to the sleeve 2, and the automation unit 28 has transducers for automatic reading of the magnitude of displacement and rotation. The read values can be fed back to the motorized actuators in order to control their operation so the desired movement of the mandrel 4 is achieved.

The values read for the displacement and rotation of the mandrel 4 are sent to a position identification unit 30 for determining the true position of the catheter's transmitter or receiver 8, and these values, with data from the receiver unit 10 representing positions for the catheter transmitter 8, are sent to an analysis unit 32. In instances in which the position location means 10 are devised as a transmitter unit for transmitting signals intended for reception by a catheter receiver 8, the signals received by the catheter receiver 8 are instead sent to the analysis unit 32.

Determination of the correction function is performed as follows:

The catheter transmitter or receiver 8 is made to perform a known movement, preferably a three-dimensional movement, in the space inside the basket 6 during simultaneous registration of the position of the catheter transmitter or receiver 8 with the measurement system which is to be calibrated, i.e. the catheter transmitters or receivers and position location unit 10. The analysis unit 32, which includes a computer system, compares the true movement made by the catheter transmitter or receiver 8, as determined from the scales 26 or by transducers in the automation unit 28, with the "apparent" or measured movement obtained with the position location unit 10. A correction function, with which the measured, apparent position of the catheter tip can be translated in a subsequent measurement stage into a true position, is calculated from the difference between the two movements. The movement can e.g. form a body with a known shape, as described by the catheter transmitter or receiver 8, whereupon the correction function is determined from the difference between this true shape and the shape determined by the position location unit 10.

The calibration procedure can use a balloon, instead of a wire basket, inside the catheter sleeve 2 during the catheter's insertion into the patient's body, the balloon thereupon being deployed outside the sleeve and inflated with a gas, e.g. air, or a liquid, e.g. isotonic saline solution or some other liquid with the appropriate physical properties. In certain instances, depending on the kind of position location system utilized, the use of a liquid with the right properties is particularly important in preventing distortion of wave fronts. This is especially the case if ultrasonic signals are employed for position location.

If a number of calibration transmitters or receivers 34 are permanently arranged on the wires of the basket, the calibration stage can be performed without the need for a mandrel, carrying a transmitter or receiver, to move the transmitter or receiver to different known positions. If the wire basket 6 is sufficiently stiff, the calibration transmitters or receivers 34 will assume known positions after expansion of the basket 6, and the correction function can be determined from the differences between these true positions and the positions measured for the transmitters or receivers 34 by the position location unit 10. When calibration transmitters or receivers are permanently arranged on the wall of a balloon, of the kind described above, the same technique can be used in this instance for determining the correction function. The balloon must be inflated with pressure sufficient for it to assume a known, well-defined shape.

After calibration, the calibration catheter can be replaced with a special measurement catheter which is inserted into the sleeve 2. Alternatively, the wire basket 6 can be arranged with an opening at its anterior end through which the mandrel 4 with its transmitter or receiver 8 can be inserted for subsequent measurement stages. Here, the mandrel 4 and wire basket 6 are first retracted into the sleeve 2, whereupon only the mandrel and its transmitter or receiver protrude through the opening in the basket.

After calibration, the same catheter, or some other catheter, can be used for e.g. mapping, as noted above. The catheter can be designed to perform a number of functions which may be needed in the diagnosis and/or treatment of various patient disorders. The catheter can be equipped with electrodes for sensing electrical activity in body tissue and/or electrical stimulation of body tissue, for ablation or be equipped with pressure sensors. The previously determined correction function is used here for positioning the catheter during the diagnostic and/or therapeutic procedures.

The position location unit, which can be devised, as noted above, as transmitters or receivers (antennae), arranged on another catheter or catheters, can be located outside the patient's body or inside her/his body. If the position location means is outside the patient's body, or inside her/his body, at a relatively long distance from the calibration and measurement catheter, compensation for movements the patient might make, e.g. in breathing, is often necessary. This can be performed by utilization of one or a number of reference catheters arranged in the vicinity of the catheter in question. When the reference catheter or catheters is/are in the vicinity of the measurement catheter, the reference catheter or catheters and measurement catheters do not move in relation to each other but only move jointly. Here, the position determination technique according to the invention can also be used for determining the positions of the reference catheters.

Alternatively, one or more reference communication elements 36 (transmitters or receivers, see FIG. 1) can be permanently arranged on the catheters 2. The detected movement of the catheter transmitter or receiver 8 in relation to these reference transmitters or receivers 36 is the "true" movement of the tip of the catheter and is therefore not caused by patient movements. In this embodiment, the catheter therefore serves as its own reference.

In certain applications, establishing a reference point for the catheter transmitter or receiver and the catheter in relation to the examined organ, e.g. a starting position or end position to which reference point the movement of the catheter is related, is desirable. One such reference point can be registered by biplane exposure with a fluoroscope or some other known technique.

The transmitters and receivers used in the invention can be piezo elements for ultrasonic position location signals, coils or antennae for electromagnetic position location signals or magnets and Hall-generators for magnetostatic communications systems.

Since the heart, blood vessels and other organs pulsate at each heartbeat, synchronizing registration of the catheter's position to the ECG signal is often necessary so each position registration occurs in the same phase of the heart cycle. This eliminates this source of error in position determination. For this reason, a synchronization unit 38 is arranged to synchronize the analysis unit 32 so it performs catheter position determinations in the same phase of the heart cycle, as shown in FIG. 1.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for detecting a position of a catheter when inside a body of a subject, comprising the steps of:

inserting a calibration catheter into a body cavity;

in a calibration phase, transmitting signals between a plurality of known calibration positions of said calibration catheter in said body cavity and a position locator, and obtaining, at said position locator, a plurality of apparent calibration positions respectively associated with said known positions but deviating therefrom due to passage of said signals through body tissue;

in said calibration phase, generating a correction function from the deviation of said apparent calibration positions from said known calibration positions; and correcting, using said correction function, subsequent signals transmitted between a medical procedure catheter in said body cavity and said position locator to obtain an identification of an actual position of said medical procedure catheter in said body cavity.

2. A method as claimed in claim 1 comprising the step of using said calibration catheter as said medical procedure catheter.

3. A method as claimed in claim 1 wherein the step of transmitting signals comprises transmitting signals from said plurality of known calibration positions of said calibration catheter in said body cavity to said position locator.

4. A method as claimed in claim 3 wherein said calibration catheter has a tip, and wherein the step of transmitting signals comprises transmitting signals between a plurality of known calibration positions of said tip of said catheter in said body cavity and said position locator.

5. A method as claimed in claim 4 comprising the additional steps of:

deploying an expandable element at said tip of said calibration catheter, said expandable element carrying a plurality of communication elements which communicate with said position locator;

expanding said expandable element after inserting said calibration catheter into said body cavity for causing said plurality of communication elements to respectively assume said plurality of known calibration positions;

retracting said expandable element after said calibration phase; and using said calibration catheter as said medical procedure catheter after said calibration phase.

6. A method as claimed in claim 1 wherein the step of transmitting signals comprises transmitting signals from said position locator to said calibration catheter at said plurality of known calibration positions in said body cavity.

7. A method as claimed in claim 1 comprising the step of physically moving said calibration catheter through a known movement in said body cavity for producing said plurality of known calibration positions.

8. A method as claimed in claim 7 wherein the step of physically moving said calibration catheter comprises physically moving said calibration catheter in said body cavity to describe a body of a known shape, and wherein the step of generating a correction function comprises deriving an apparent body shape from said apparent calibration positions and determining said correction function from a deviation of said apparent body shape from said known body shape.

9. A method as claimed in claim 8 comprising the additional step of identifying a reference position of said calibration catheter at a beginning of said physical movement using a biplane exposure obtained with a fluoroscope.

10. A method as claimed in claim 7 wherein the step of physically moving said calibration catheter comprises physically moving said calibration catheter in said body cavity to describe a surface of a known shape, and wherein the step of generating a correction function comprises deriving an apparent surface shape from said apparent calibration positions and determining said correction function from a deviation of said apparent surface shape from said known surface shape.

11. A method as claimed in claim 10 comprising the additional step of identifying a reference position of said calibration catheter at a beginning of said physical movement using a biplane exposure obtained with a fluoroscope.

12. An apparatus for detecting a position of a catheter when inside a body of a patient, comprising:
a calibration catheter adapted for insertion into a body cavity;
a position locator;
means for transmitting signals, in a calibration phase, between a plurality of known calibration positions of said calibration catheter in said body cavity and said position locator;
said position locator comprising means for obtaining a plurality of apparent calibration positions respectively associated with said known positions but deviating therefrom due to passage of said signals through body tissue;
means, in said calibration phase, for generating a correction function from the deviations of said apparent calibration positions from said known calibration positions;
a medical procedure catheter for conducting a medical procedure, subsequent to said calibration phase, in said body cavity, and means for transmitting signals between said medical procedure catheter and said position locator while said medical procedure catheter is in said body cavity, said position locator comprising means for identifying an apparent position of said medical procedure catheter in said body cavity from said signals transmitted between said medical procedure catheter and said position locator; and
means for correcting said apparent position of said medical procedure catheter, using said correction function, to identify an actual position of said medical procedure catheter in said body cavity.

13. An apparatus as claimed in claim 12 wherein said medical procedure catheter and said calibration catheter comprise a single catheter, and wherein said single catheter carries a transmitter arrangement operating in common as said means for transmitting signals between said medical procedure catheter and said position locator, and said means for transmitting signals between said plurality of known calibration positions and said position locator.

14. An apparatus as claimed in claim 12 wherein said means for transmitting signals comprises a transmitter disposed at said calibration catheter and a receiver disposed at said position locator.

15. An apparatus as claimed in claim 12 wherein said means for transmitting comprises a transmitter disposed at said position locator and a receiver disposed at said calibration catheter.

16. An apparatus as claimed in claim 12 wherein said means for transmitting signals includes a communication element carried by said calibration catheter for communicating via said signals with said position locator, and wherein said calibration catheter comprises a flexible, tubular outer sleeve and a mandrel slidably and rotatably disposed in said sleeve, said mandrel having a tip at which said communication element is disposed.

17. An apparatus as claimed in claim 16 wherein said mandrel has an end section, deployable beyond an end of said sleeve, said end section of said mandrel comprising resilient material and being pre-bent.

18. An apparatus as claimed in claim 16 wherein said mandrel has an end deployable beyond an end of said sleeve, and comprises a curved coil spring attached at said end of said mandrel and having an opposite end at which communication element is disposed.

19. An apparatus as claimed in claim 16 wherein said mandrel has an end section deployable beyond an end of said sleeve, said end section comprising a memory alloy, and wherein said calibration catheter includes means for electrically heating said end section of said mandrel to cause said memory alloy to bend.

20. An apparatus as claimed in claim 16 wherein said mandrel has an end section deployable beyond an end of said sleeve, said end section of said mandrel comprising a mechanical joint permitting bending of said end section.

21. An apparatus as claimed in claim 16 wherein said mandrel is deployable beyond a first end of said sleeve, and wherein said sleeve has a second, opposite end at which means for manipulating said mandrel relative to said sleeve are disposed, said means for manipulating comprising means for at least of one sliding said mandrel and rotating said mandrel in said sleeve.

22. An apparatus as claimed in claim 21 wherein said means for manipulating comprise means for sliding said mandrel relative to said sleeve and wherein said means for manipulating include indicator means for displaying a magnitude of sliding of said mandrel relative to said sleeve.

23. An apparatus as claimed in claim 21 wherein said means for manipulating comprise means for rotating said mandrel relative to said sleeve and wherein said means for manipulating include indicator means for displaying a magnitude of rotating of said mandrel relative to said sleeve.

24. An apparatus as claimed in claim 21 wherein said means for manipulating comprise means for sliding and rotating said mandrel relative to said sleeve and wherein said means for manipulating include indicator means for displaying a magnitude of sliding and rotating of said mandrel relative to said sleeve.

25. An apparatus as claimed in claim 21 wherein said means for manipulating comprises means for motorized manipulating of said mandrel.

26. An apparatus as claimed in claim 25 wherein said means for motorized manipulating comprises a controllable drive motor and a transducer, connected to said controllable drive motor, for monitoring a degree of manipulation of said mandrel and for controlling said drive motor dependent on said degree of manipulation.

27. An apparatus as claimed in claim 16 further comprising an expandable element disposed at said tip of said mandrel, on which said communication element is disposed, said expandable element being deployable by said mandrel beyond an end of said sleeve.

28. An apparatus as claimed in claim 27 wherein said expandable element comprises a balloon, and wherein said calibration catheter includes means for inflating said balloon in said body cavity after said balloon is deployed beyond said end of said sleeve.

29. An apparatus as claimed in claim 27 wherein said expandable element comprises a basket which resiliently expands in said body cavity upon deployment beyond said end of said sleeve.

30. An apparatus as claimed in claim 27 wherein said expandable element is retractable, after said calibration phase, into said sleeve for allowing said end of said sleeve, after said calibration phase, to contact body tissue.

31. An apparatus as claimed in claim 12 wherein said means for transmitting signals includes a communication element carried by said calibration catheter which communicates via said signals with said position locator, and wherein said calibration catheter comprises an outer catheter sleeve having an end adapted for insertion in said body cavity, and an expandable element contained in said sleeve and deployable, in an expanded condition, beyond said end of said sleeve in said body cavity, said communication element being disposed on said expandable element.

32. An apparatus as claimed in claim 31 wherein said expandable element comprises a balloon, and wherein said calibration catheter includes means for expanding said balloon when said balloon is deployed beyond said end of said catheter in said body cavity.

33. An apparatus as claimed in claim 31 wherein said expandable element comprises a resilient basket which resiliently expands in said body cavity upon deployment beyond said end of said sleeve.

34. An apparatus as claimed in claim 12 wherein said medical procedure catheter comprises and said calibration catheter comprise a single catheter, and wherein said single catheter carries means for interacting with body tissue in said body cavity selected from the group consisting of stimulation electrodes, sensing electrodes, ablation equipment and pressure sensors.

35. An apparatus as claimed in claim 12 wherein each of said means for transmitting signals in said calibration phase and said means for transmitting signals between said medical procedure catheter and said position locator comprise means for ultrasonically transmitting signals.

36. An apparatus as claimed in claim 12 wherein each of said means for transmitting signals in said calibration phase and said means for transmitting signals between said medical procedure catheter and said position locator comprise means for electromagnetically transmitting signals.

37. An apparatus as claimed in claim 12 wherein each of said means for transmitting signals in said calibration phase and said means for transmitting signals between said medical procedure catheter and said position locator comprise means for magnetostatically transmitting signals.

38. An apparatus as claimed in claim 12 further comprising synchronization means for synchronizing said means for correcting for always identifying said actual position of said medical procedure catheter at a same phase of a heart cycle of said subject.

39. An apparatus as claimed in claim 12 further comprising a reference communication element, in communication with said position locator, for producing a reference signal identifying movement of said subject, and wherein said means for generating a correction function comprises means for generating a correction function dependent on said apparent calibration positions and said reference signal.

* * * * *